United States Patent
Kim (10) Patent No.: US 9,920,457 B2
(45) Date of Patent: Mar. 20, 2018

(54) METHOD FOR MANUFACTURING CORD YARN WITH EXCELLENT DIMENSIONAL STABILITY

(71) Applicant: Il Han Kim, Daegu (KR)

(72) Inventor: Il Han Kim, Daegu (KR)

( * ) Notice: Subject to any disclaimer, the term of this patent is extended or adjusted under 35 U.S.C. 154(b) by 291 days.

(21) Appl. No.: 14/657,577

(22) Filed: Mar. 13, 2015

(65) Prior Publication Data

US 2015/0240395 A1    Aug. 27, 2015

Related U.S. Application Data

(63) Continuation of application No. PCT/KR2013/006352, filed on Jul. 16, 2013.

(30) Foreign Application Priority Data

Jan. 28, 2013 (KR) .......................... 10-2013-0009234

(51) Int. Cl.
| | |
|---|---|
| *D02G 3/28* | (2006.01) |
| *D02G 3/02* | (2006.01) |
| *D02G 3/26* | (2006.01) |
| *A01K 91/00* | (2006.01) |
| *A61C 15/04* | (2006.01) |

(52) U.S. Cl.
CPC .............. *D02G 3/28* (2013.01); *A01K 91/00* (2013.01); *A61C 15/041* (2013.01); *D02G 3/02* (2013.01); *D02G 3/26* (2013.01)

(58) Field of Classification Search
CPC .............. D02G 3/02; D02G 3/26; D02G 3/28
See application file for complete search history.

(56) References Cited

U.S. PATENT DOCUMENTS

| | | | | |
|---|---|---|---|---|
| 1,825,071 A | * | 9/1931 | Kayser | ..................... D02G 3/24 |
| | | | | 28/154 |
| 3,419,059 A | * | 12/1968 | Bridge, Jr. | ............ B60C 9/0042 |
| | | | | 152/451 |

(Continued)

FOREIGN PATENT DOCUMENTS

| | | |
|---|---|---|
| GB | 2022154 A | 12/1979 |
| JP | 08246281 A | 9/1996 |

(Continued)

OTHER PUBLICATIONS

The above foreign references were cited in a Supplementary European Search Report dated Dec. 21, 2016, that issued in the corresponding European Patent Application No. 13872607.0.

(Continued)

*Primary Examiner* — Shaun R Hurley
(74) *Attorney, Agent, or Firm* — Cowan, Liebowitz & Latman P.C.

(57) ABSTRACT

A method for manufacturing a cord yarn, which has at least one filament strand, includes applying a first twist so that a K1 value has a value of 0.1837763/D1n or below, applying a second twist so that a K2 value has a value between 0.0166819/D2n and 0.3183099/D2n, and applying a third twist so that a K3 value has a value between 0.0278485/D3 and 0.2968288/D3, wherein the twists are applied so that the cord yarn has roundness of 50% or above, and when the filament is a multi filament, so that porosity between strands of the cord yarn is less than 40%.

15 Claims, 8 Drawing Sheets

(56) References Cited

U.S. PATENT DOCUMENTS

| | | | | |
|---|---|---|---|---|
| 3,422,873 | A | * | 1/1969 | Liska .................... B60C 9/0042 |
| | | | | 152/556 |
| 4,877,073 | A | * | 10/1989 | Thise .................... B60C 9/0042 |
| | | | | 152/451 |
| 5,397,527 | A | | 3/1995 | Rim et al. |
| 7,263,820 | B2 | | 9/2007 | Rim et al. |
| 2002/0166316 | A1 | * | 11/2002 | Mills ...................... D02G 3/445 |
| | | | | 57/293 |
| 2003/0152757 | A1 | * | 8/2003 | Van Campen ........... D02G 3/28 |
| | | | | 428/292.1 |
| 2009/0071117 | A1 | * | 3/2009 | Hegan, Jr. ................ D02G 3/28 |
| | | | | 57/230 |
| 2013/0291286 | A1 | * | 11/2013 | Stuckey .................. D02G 1/02 |
| | | | | 2/243.1 |

FOREIGN PATENT DOCUMENTS

| | | |
|---|---|---|
| KR | 10-1994-0014945 | 7/1994 |
| KR | 20-1998-0065555 | 12/1998 |
| KR | 10-1999-0031886 | 5/1999 |
| KR | 10-2002-0061368 | 7/2002 |
| KR | 10-0846197 | 7/2008 |

OTHER PUBLICATIONS

The above US and Foreign patent documents 3, 4, and 5 were cited the International Search Report of PCT/KR2013/006352 dated Oct. 29, 2013.

* cited by examiner

FIG. 1

A: MULTI OR MONO FILAMENT
D1: DIAMETER (m) OF FIBER A
K1: NUMBER OF BRAIDS (/m)
1/K1: LENGTH (m) OF ONE BRAID
Θ1: BRAID ANGLE
πD: CIRCUMFERENCE OF FIBER A

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | porosity | number | specific | ⌀ave | # | |
| 1 | 492.0 d | 323.4 μm | 176.4 μm | 255.3 μm | 13.5 μm | 66.8% | 66,582 μm2 | 14.8% | 1045 | 3.59 | 281.2 μm | 3.085 | 109.0 |
| 2 | 492.3 d | 323.9 μm | 176.3 μm | 255.1 μm | 13.6 μm | 66.5% | 66,563 μm2 | 14.8% | 996 | 3.43 | 291.1 μm | 3.084 | 108.9 |
| 3 | 498.9 d | 324.0 μm | 176.2 μm | 255.2 μm | 13.5 μm | 66.5% | 66,544 μm2 | 14.7% | 1023 | 3.51 | 291.1 μm | 3.084 | 108.9 |
| Ave. | 494.4 d | 323.8 μm | 176.3 μm | 255.2 μm | 13.5 μm | 66.6% | 66,563 μm2 | 14.8% | 954 | 3.51 | 291.1 μm | 3.084 | 108.9 |
| mono Fil. | 494.6 d | 267.2 μm | 267.2 μm | 267.2 μm | 0.0 μm | 100.0% | 56,729 μm2 | 0.0% | | | 267.2 μm | 2.582 | 100.0 |

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | Porosity | number | specific | d ave | # | |
| 1 | 304.0 d | 261.5 μm | 156.4 μm | 214.2 μm | 24.6 μm | 75.8% | 37,386 μm2 | 7.6% | 966 | 4.43 | 218.2 μm | 1.721 | 104.1 |
| 2 | 304.0 d | 261.4 μm | 156.0 μm | 214.0 μm | 24.8 μm | 75.7% | 37,287 μm2 | 7.6% | 924 | 4.24 | 217.9 μm | 1.717 | 104.0 |
| 3 | 304.0 d | 261.4 μm | 156.2 μm | 214.2 μm | 24.8 μm | 75.9% | 37,336 μm2 | 7.7% | 972 | 4.46 | 218.0 μm | 1.719 | 104.1 |
| Ave. | 304.0 d | 261.5 μm | 156.2 μm | 214.1 μm | 24.7 μm | 75.8% | 37,336 μm2 | 7.7% | 954 | 4.38 | 218.0 μm | 1.719 | 104.1 |
| mono Fil. | 304.0 d | 209.5 μm | 209.5 μm | 209.5 μm | 0.0 μm | 100.0% | 34,467 μm2 | 0.0% | | | 209.5 μm | 1.587 | 100.0 |

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | Porosity | number | specific | Φave | # | |
| 1 | 232.0 d | 221.2 μm | 104.2 μm | 178.2 μm | 9.3 μm | 56.9% | 27,715 μm2 | 5.1% | 688 | 3.66 | 187.9 μm | 1.276 | 102.6 |
| 2 | 232.0 d | 221.2 μm | 104.2 μm | 178.2 μm | 8.2 μm | 56.9% | 27,715 μm2 | 5.1% | 722 | 3.84 | 187.9 μm | 1.276 | 102.6 |
| 3 | 232.0 d | 221.2 μm | 104.2 μm | 178.2 μm | 8.7 μm | 56.9% | 27,715 μm2 | 5.1% | 692 | 3.68 | 187.9 μm | 1.276 | 102.6 |
| Ave. | 232.0 d | 221.2 μm | 104.2 μm | 178.2 μm | 8.7 μm | 56.9% | 27,715 μm2 | 5.1% | 701 | 3.73 | 187.9 μm | 1.276 | 102.6 |
| mono Fil. | 232.0 d | 183.0 μm | 183.0 μm | 183.0 μm | 0.0 μm | 100.0% | 26,304 μm2 | 0.0% | | | 183.0 μm | 1.211 | 100.0 |

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | Porosity | number | specific | Φave | # | |
| 1 | 56.8 d | 67.6 μm | 33.7 μm | 48.7 μm | 8.3 μm | 61.6% | 7,761 μm2 | 16.8% | 223 | 2.24 | 99.6 μm | 0.358 | 109.6 |
| 2 | 56.9 d | 60.3 μm | 29.1 μm | 46.9 μm | 9.0 μm | 55.7% | 7,568 μm2 | 14.5% | 231 | 2.35 | 98.2 μm | 0.346 | 108.1 |
| 3 | 57.5 d | 62.0 μm | 34.9 μm | 47.6 μm | 8.7 μm | 57.6% | 7,671 μm2 | 15.6% | 228 | 2.31 | 98.8 μm | 0.353 | 108.9 |
| Ave. | 57.1 d | 63.3 μm | 32.6 μm | 47.7 μm | 8.7 μm | 58.3% | 7,673 μm2 | 15.6% | 227 | 2.30 | 98.8 μm | 0.353 | 108.9 |
| mono Fil. | 57.1 d | 90.8 μm | 90.8 μm | 90.8 μm | 0.0 μm | 100.0% | 6,474 μm2 | 0.0% | | | 90.8 μm | 0.298 | 100.0 |

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | Porosity | number | specific | ave | # | |
| 1 | 304.3 d | 294.7 μm | 134.2 μm | 213.5 μm | 33.4 μm | 43.5% | 58,492 μm2 | 42.0% | 476 | 1.74 | 272.9 μm | 2.693 | 130.2 |
| 2 | 304.6 d | 294.7 μm | 134.8 μm | 213.4 μm | 33.5 μm | 43.9% | 58,485 μm2 | 42.0% | 465 | 1.70 | 272.9 μm | 2.693 | 130.2 |
| 3 | 304.5 d | 294.6 μm | 134.6 μm | 213.4 μm | 33.4 μm | 43.9% | 58,398 μm2 | 41.9% | 488 | 1.79 | 272.7 μm | 2.688 | 130.1 |
| Ave. | 304.5 d | 294.6 μm | 134.5 μm | 213.4 μm | 33.4 μm | 43.7% | 58,458 μm2 | 42.0% | 476 | 1.76 | 272.8 μm | 2.691 | 130.1 |
| mono Fil. | 304.5 d | 209.7 μm | 209.7 μm | 209.7 μm | 0.0 μm | 100.0% | 33,907 μm2 | 0.0% | | | 209.7 μm | 1.589 | 100.0 |

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | Porosity | number | specific | ave | # | |
| 1 | 304.3 d | 287.6 μm | 145.8 μm | 217.8 μm | 27.6 μm | 57.6% | 57,392 μm2 | 42.7% | 522 | 1.93 | 270.3 μm | 2.642 | 128.9 |
| 2 | 304.6 d | 287.4 μm | 145.8 μm | 217.8 μm | 27.6 μm | 57.7% | 57,366 μm2 | 42.7% | 515 | 1.91 | 270.3 μm | 2.642 | 128.9 |
| 3 | 304.5 d | 287.6 μm | 145.8 μm | 217.8 μm | 27.6 μm | 57.6% | 57,373 μm2 | 42.7% | 521 | 1.93 | 270.3 μm | 2.641 | 128.9 |
| Ave. | 304.5 d | 287.5 μm | 145.8 μm | 217.8 μm | 27.6 μm | 57.7% | 57,384 μm2 | 42.7% | 519 | 1.92 | 270.3 μm | 2.642 | 128.9 |
| mono Fil. | 304.5 d | 209.7 μm | 209.7 μm | 209.7 μm | 0.0 μm | 100.0% | 32,890 μm2 | 0.0% | | | 209.7 μm | 1.589 | 100.0 |

| No. | Denier | Roundness | | | | | Porosity | | Abrasion | | Size | | Ratio |
|---|---|---|---|---|---|---|---|---|---|---|---|---|---|
| | | dist max | dist min | dist ave | dist sd | roundness | pixel area | Porosity | number | specific | $\Phi$ave | $\sigma$ | |
| 1 | 301.6 d | 295.3 $\mu$m | 124.2 $\mu$m | 216.5 $\mu$m | 27.6 $\mu$m | 37.5% | 58,432 $\mu$m2 | 44.7% | 354 | 1.30 | 272.8 $\mu$m | 2.690 | 130.7 |
| 2 | 301.5 d | 295.3 $\mu$m | 124.3 $\mu$m | 216.5 $\mu$m | 27.6 $\mu$m | 37.6% | 58,463 $\mu$m2 | 44.7% | 329 | 1.21 | 272.8 $\mu$m | 2.692 | 130.8 |
| 3 | 301.5 d | 295.4 $\mu$m | 124.2 $\mu$m | 216.5 $\mu$m | 27.6 $\mu$m | 37.5% | 58,419 $\mu$m2 | 44.6% | 372 | 1.36 | 272.7 $\mu$m | 2.690 | 130.7 |
| Ave. | 301.5 d | 295.3 $\mu$m | 124.2 $\mu$m | 216.5 $\mu$m | 27.6 $\mu$m | 37.5% | 58,438 $\mu$m2 | 44.7% | 352 | 1.29 | 272.8 $\mu$m | 2.690 | 130.7 |
| mono Fil. | 301.5 d | 208.8 $\mu$m | 208.8 $\mu$m | 208.8 $\mu$m | 0.0 $\mu$m | 100.0% | 32,340 $\mu$m2 | 0.0% | | | 208.8 $\mu$m | 1.574 | 100.0 |

FIG. 23

METHOD FOR MANUFACTURING CORD YARN WITH EXCELLENT DIMENSIONAL STABILITY

TECHNICAL FIELD

The present disclosure relates to a cord, yarn useable for a kite line, a line for adjusting a blind, a fishing line, a high-strength industrial string, a floss, a parachute cord or the like, and more particularly, to a high-strength cord yarn with excellent dimensional stability, which may be extensively used in the industries without being limited to the above due to thin design, great tenacity, good abrasion resistance, and excellent dimensional stability.

BACKGROUND ART

In order to manufacture a cord yarn with thin design, great tenacity and excellent dimensional stability, various methods such as braiding, knitting using a needle, covering, simple twisting or the like have been widely used. However, because the structure not delicate, the cord yarn made by the above methods has high porosity, and a product formed with several strands has very low roundness.

Therefore, such a cord yarn has bad specific strength and a wide and flat shape, and its section is flattened more if a force is applied thereto.

In addition, Korean Unexamined Patent Publication No. 20-1998-0065555, published on Dec. 5, 1998, discloses a structure of a tire cord yarn, which however is different from a cord yarn of the present disclosure in which a plurality of filaments are twisted appropriately.

Moreover, Korean Patent Registration No. 10-0846197, published on Jul. 14, 2008, discloses a cord yarn supplying device for an embroidering machine and a cord yarn sealing method, which is also different from a cord yarn of the present disclosure in which a plurality of filaments are twisted appropriately.

DISCLOSURE

Technical Problem

In order to manufacture a cord yarn with thin design, great tenacity and excellent dimensional stability, the followings are required: as Feature 1, a method for maximizing intensity of a single yarn is required; as Feature 2, the number of twists should be suitably set in a second twisting step and a third twisting step so that the breaking, strength of the cord yarn does not deteriorate; as Feature 3, the roundness should be close to 1; and as Feature 4, the smaller porosity the better.

Technical Solution

In one aspect of the present disclosure, there is provided a method for manufacturing a cord yarn, which has at least one filament strand, the method including: applying a first twist (a first twisting step) so that a K1 value has a value of $0.1837763/D1$ or below; applying a second twist (a second twisting step) so that a K2 value has a value between $0.0166819/D2$ and $0.3183099/D2$; and applying a third twist (a third twisting step) so that a K3 value has a value between $0.0278485/D3$ and $0.2968288/D3$, wherein the twists are applied so that the cord yarn has roundness of 50% or above, and when the filament is a multi filament, so that porosity between strands of the cord yarn is less than 40%.

In addition, in the present disclosure, before each twisting step, the filament may be guided by a positioning device.

In addition, in the present disclosure, in each twisting step, a twist may be applied together with elongation of 1 to 20%.

In addition, in the present disclosure, when the filament is a multi filament, fineness of a single filament may be 0.5 denier to 10 denier, fineness of the entire filament may be 3 denier to 2,400 denier, and a filament yarn may be any one of nylon, polyester, polyethylene including ultrahigh molecular weight polyethylene, aramid, p-phenylene benzobisoxazole (PBO), polyketon, polyacrylate fiber and polyvinyl alcohol (PVA) fiber which are 5 g/d or above in a breaking strength. In addition, when the filament is a mono filament, fineness may be 3 denier to 2,400 denier, and a yarn of the filament may be any one of nylon, polyester, polyethylene including ultrahigh molecular weight polyethylene, polyphenylene sulfide (PPS) and polyvinylidene fluoride (PVDF) which are 5 g/d or above in a breaking strength, and polytetrafluoroethylene (PTFE) having a breaking strength of 3 g/d or above.

In addition, in the present disclosure, when the filament is guided by a positioning device in any one of the twisting steps, at least one strand having a breaking strength of 2 g/d or above of PTFE with, melamine yarn, carbon fiber, metal thread or polymer thread fused at 200° C. or below may be guided by the positioning device to be located at the center of the cord yarn.

In another aspect of the present disclosure, there is also provided a cord yarn, which has at least one filament strand, the cord yarn including a first twist having a K1 value of $0.1837763/D1n$ or below; a second twist having a K2 value between $0.0166819/D2n$ and $0.3183099/D2n$; and a third twist having a K3 value between $0.0278485/D3$ and $0.2968288/D3$, wherein the cord yarn has roundness of 50% or above.

In addition, in the present disclosure, when the filament is a multi filament, porosity between strands of the cord yarn may be less than 40%.

In addition, in the present disclosure, at least one strand having a breaking strength of 2 g/d or above of PTFE, melamine yarn, carbon fiber, metal thread or polymer thread fused at 200° C. or below may be located at the center of the cord yarn to allow specific weight adjustment, fusion, or both specific weight adjustment and fusion.

In addition, in the present disclosure, the cord yarn or a product obtained by coating, water-repelling or silicon-treating the cord yarn may be applied to fabric, knit works, strings, fishing lines, ropes, accessories for mobile phones, floss, parachute cords or lines for adjusting blinds.

Advantageous Effects

The cord yarn according to the present disclosure is useable for a kite line, a line for adjusting a blind, a fishing line, a high-strength industrial string, a floss, a parachute cord or the like, and particularly, it is possible to manufacture a high-strength cord yarn with excellent dimensional stability, which tray be extensively used in the industries without being limited to the above due to thin design, great tenacity, good abrasion resistance, and excellent dimensional stability.

BEST MODE

The present disclosure is directed to manufacturing a cord yarn excellent in tenacity and abrasion resistance, and a suitable number of twists are endowed in a single step in order to maximize tenacity of a single yarn.

Figure 1:
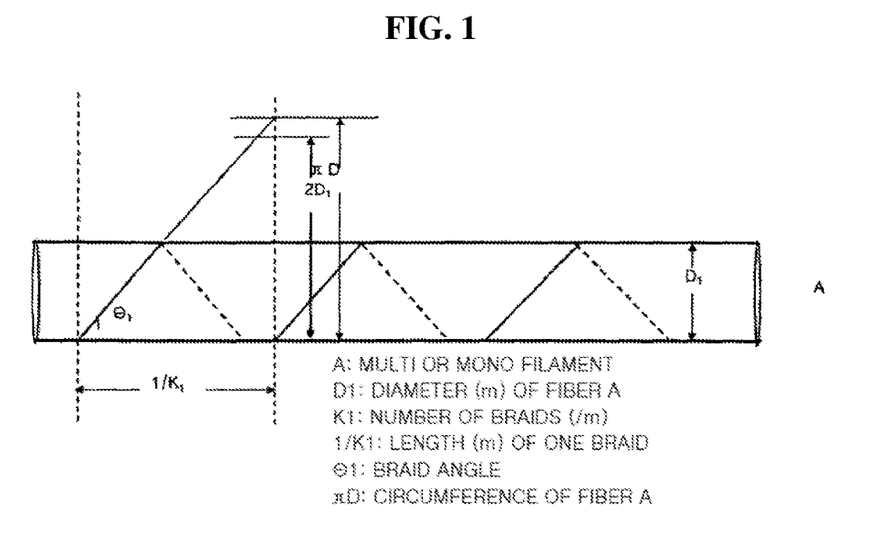
FIG. 1 is a diagram for illustrating a twist of the present disclosure.

FIG. 1 is to explain terms used in the present disclosure. Here, A represents a multi or mono filament, D1 represents a diameter (m) of a fiber A, K1 represents the number of braids per unit length (/m), 1/K1 represents a length (m) of one braid, $\Theta 1$ represents a braid angle, and $\pi D$ represents a circumference of the fiber A.

Figure 2:
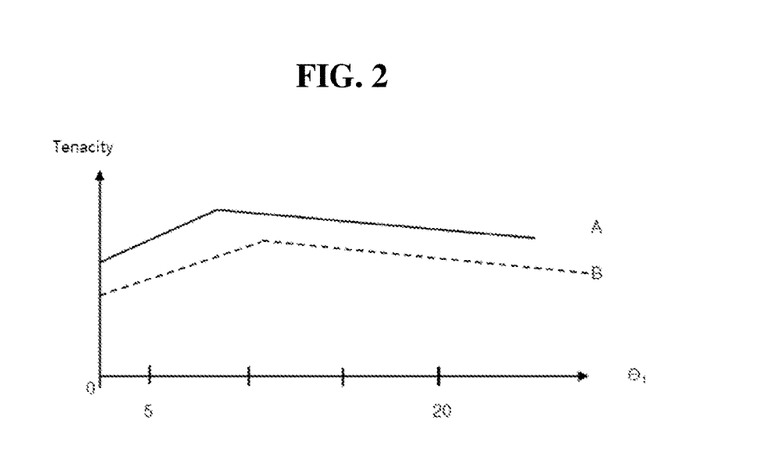
FIG. 2 is a diagram for illustrating a relation between a braid angle and tenacity of a single yarn during a twisting process.

A twist angle according to diameter and twist of a fiber may be expressed like FIG. 1, and tenacity according to a twist has a tendency as shown in FIG. 2.

In FIG. 1, $$\tan(\Theta 1) = \pi D 1 K 1, \text{ and thus } K1 = \tan(\Theta 1)/(\pi D 1) \quad \text{(Equation 1)}.$$

In addition, FIG. 2 is a graph showing a relation between $\Theta 1$ and intensity tenacity. Here, it may be understood that tenacity increases when $\Theta 1$ is in a region of 0.1 degree to 15 degrees and then decreases like lines A and B.

Therefore, if the range of $\Theta 1$ from 0.1 degree to 15 degrees is applied to Equation 1, a K1 value may be obtained like $0.0005556/D1 \leq K1 \leq 0.1837763/D1$ [K1=the number of twists per meter, D1=diameter (m) on the assumption that a single strand has a circular section].

In addition, more preferably, in the range of $\Theta 1$ from 1 degree to 12 degrees, tenacity is maximized, and if this is applied to Equation 1, $0.0055561/D1 \leq K1 \leq 0.0676589/D1$.

Figure 3:
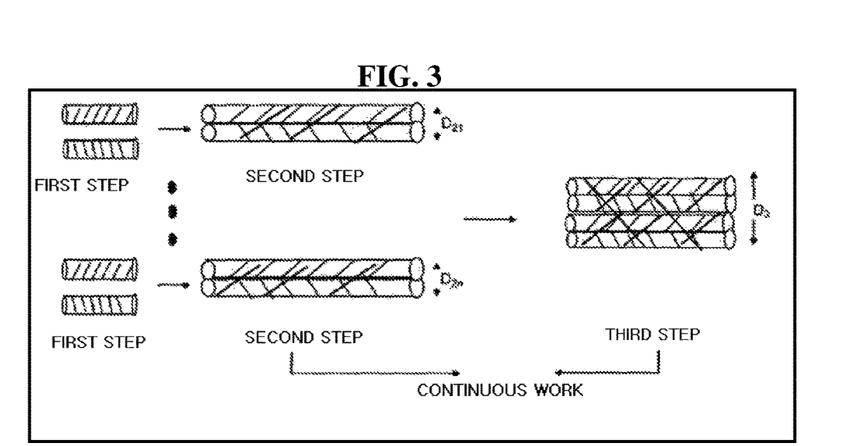
FIG. 3 is a diagram for illustrating a process for adding a twist in the present disclosure.

As Feature 2 of the present disclosure, as shown in FIG. 3, two or more strands (at least one first strand), which have been prepared in a first step (forming a first strand) to which Feature 1 is applied, should be twisted continuously in a second step and a third step. Here, the number of twists (K2) in the second step and the number of twists (K3) in the third step should be determined to maximize tenacity. In addition, the twist direction of the third step should be opposite to the twist direction of the second step so that a final residual torque (a phenomenon in which a twist is not entirely offset but remains to cause rotation) becomes close to 0.

In addition, the second step may use a single strand or several strands (at least one first strand) provided in the first step in forming a twisted strand. If a single strand is used, an additional twist is applied in the same direction as the twist direction of the first step. If several strands are used, at least one strand among the several strands should be twisted in a direction opposite to the twist direction of the other strands in the first step so that the sum of torques of all strands becomes close to 0.

Moreover, in the second step, it is important to apply the same number of twists to the strands provided in the first step in the same direction (forming a plurality of second strands).

If twists of the strands are applied in different directions from each other in the second step, a residual torque may be generated in the twist applied in the third step, or the twisted strand of the third step has a very irregular shape.

The number of twists applied in the second step may be selected to meet the following equation.

$$0.0166819/D2n \leq K2 \leq 0.2670937/D2n$$

In addition, if $\tan(\Theta)$ exceeds 1, an excessive twist is generated at an appearance of the cord yarn, which greatly deteriorates tenacity. Therefore, $\tan(\Theta)$ may be set not to exceed 1.

The number of twists applied in the third step may be selected to meet the following equation.

$$0.0278485/D3 \leq K3 \leq 0.2228830/D3$$

In addition, if the K3 value exceeds 0.13183099/D3, an excessive s is generated to greatly deteriorate tenacity, even though the appearance of the cord yarn becomes uniform.

In the second step to which Feature 2 is applied, if the K2 value is set over 0.2670937/D2, tenacity of a final product greatly deteriorates. In addition, if the K2 value is set to be 0.0166819/D2 or below, roundness deteriorates lower than 50%, and porosity also rapidly increases over 40%.

In the third step to which Feature 2 is applied, if the K3 value is set ti be 0.2228830/D3 or above, a final product has greatly deteriorated tenacity, even though its appearance is smooth.

In addition, if the K3 value is set below 0.0278485/D3, roundness deteriorates lower than 50%, porosity increases over 40%, and a residual torque is also generated.

Moreover, a twist may be applied by using an air nozzle, using a spindle, or rotating a bobbin. In order to obtain satisfactory quality, it is also possible to connect nozzles in three stages in series in order to allow continuous works. In addition, a device for rotating a spindle and a device for rotating a bobbin may be combined in use.

In addition, after the twist of the first step is applied separately, the second step and the third step may be performed continuously.

However, if processes are divided for each step in a batch type and twists are applied separately, a residual torque may not be easily managed, and thus it is very difficult to implement the present disclosure. Nevertheless, this modification is not excluded from the scope of the present disclosure.

Figure 4:
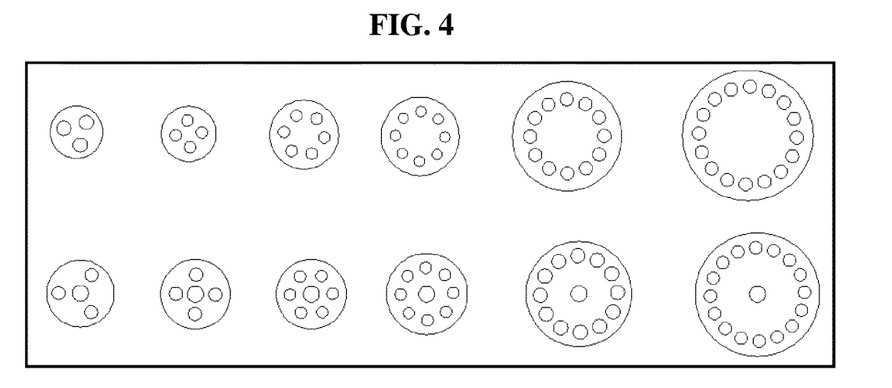
FIG. 4 is a design for illustrating a positioning device employed in the present disclosure.
Figure 5:
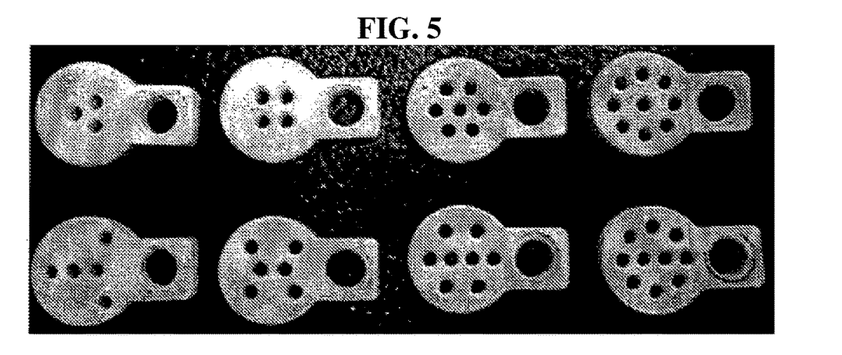
FIG. 5 is a diagram showing the positioning device employed in the present disclosure.

The roundness of Feature 3 depends on whether supplied threads are uniformly disposed and the threads are guided to the end until twists are applied thereto. In addition, the inventors have designed a special positioning device made of ceramic material (see FIG. 4), and FIG. 5 shows a positioning device actually fabricated according to a design drawing.

The roundness has a close relation with dimensional stability of a final product. If the roundness is low, the final product may spread laterally.

The roundness also has a close relation with the number of twists in the second step and the number of twists in the third step. If the number of twists in the second step and the number of twists in the third step are too high, tenacity rapidly deteriorates. If the number of twists in the second step and the number of twists in the third step are too low, a final product spreads laterally.

As the roundness increases, a draping property of the cord yarn is enhanced, and a flying distance of a fishing line increases.

In addition, as the roundness increases, a contact area of a parachute line, floss, a line for a blind or the like decreases and becomes uniform, which enhances abrasion resistance.

If the roundness is 50% or below, specific strength deteriorates as much, which makes it impossible to obtain the cord yarn according to the present disclosure.

In the present disclosure, the roundness is calculated using the following equation.

roundness=(maximum distance of a section−minimum distance of a section)$^2$/(mean distance of the section)>50% (this equation is used to measure circularity of mineral)

In addition, in order to easily find the porosity and the roundness of Features 3 and 4, a program allowing pixel-based analysis has been made.

Figure 6:
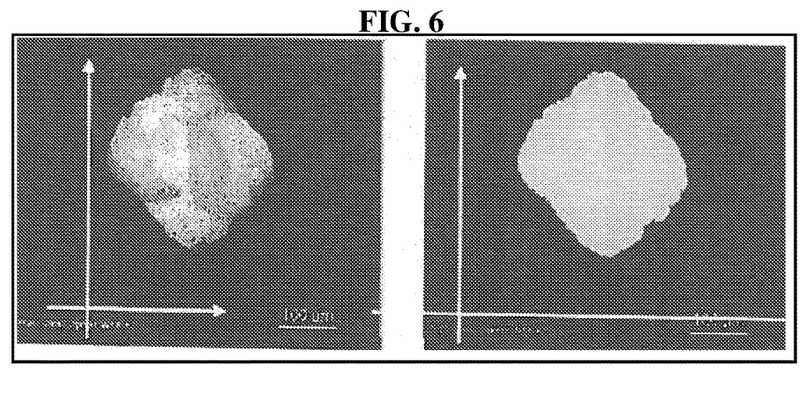
FIG. 6 is a projected sectional view for calculating roundness in the present disclosure.

Here, a camera with about 5 million pixels is attached to an optical microscope, then a section of a test piece is clearly photographed, and then the photograph is projected to an XY coordinate as shown in FIG. 6.

Since the photograph of the section is entirely displayed as pixels, a central point may be obtained by calculating a mean value of distances from any fixed reference point to every pixel. A small black point in the center of the right photograph of FIG. 6 represents the central point.

The central point is rotated by an angle of 0.01 degree, and then a line is drawn from the central angle with an angle of 0.01 degree. After that, a distance from the central point to a circumference of the cross section is measured.

This process repeats to measure distances till 360 degrees, which gives 36,000 distances, and these distances are averaged to calculate a mean radius.

In this way, a cross sectional area may be calculated even though the cord yarn has an irregular cross section.

Figure 7:
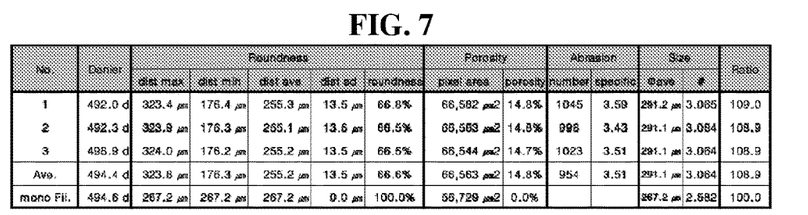
FIG. 7 is a table showing roundness calculated with respect to a section of a test piece of FIG. 6.

From the cross sectional area measured as above, the roundness is calculated as shown in the table of FIG. 7, and the porosity is also calculated.

Regarding the porosity of Feature 4, assuming that the cross sectional area is 100 when the cord yarn of the present disclosure is a mono filament with no vacancy, if an actual cross sectional area of a product of the present disclosure is measured as 150 by using a measuring program made by the inventors, the porosity is defined as (150−100)/150× 100%=33.3%.

If the porosity becomes 40% or above, the specific strength deteriorates as much, and thus it is difficult to obtain the cord yarn of the present disclosure.

porosity=$(A-B)/A \times 100 < 40\%$ (5)

A: Cross sectional area of a cord yarn calculated using a measuring program

B: Cross sectional area of a mono filament having the same denier as a test piece (calculated with specific weight and denier)

In addition, it has also been found that the porosity may be lowered further if twists are applied together with elongation of 1 to 20% for enhancing a tension of the thread during the first, second and third steps.

Moreover, in order to measure abrasion resistance of the cord yarn according to the present disclosure which sufficiently satisfies Features 1 to 4 above, a separate device has been prepared.

The cord yarn of the present disclosure is mainly used as a fishing line, and a comparative friction test was performed to the cord yarn of the present disclosure and a comparative cord yarn with the same thickness as the present disclosure by using a rubber such as ceramic.

Figure 8:
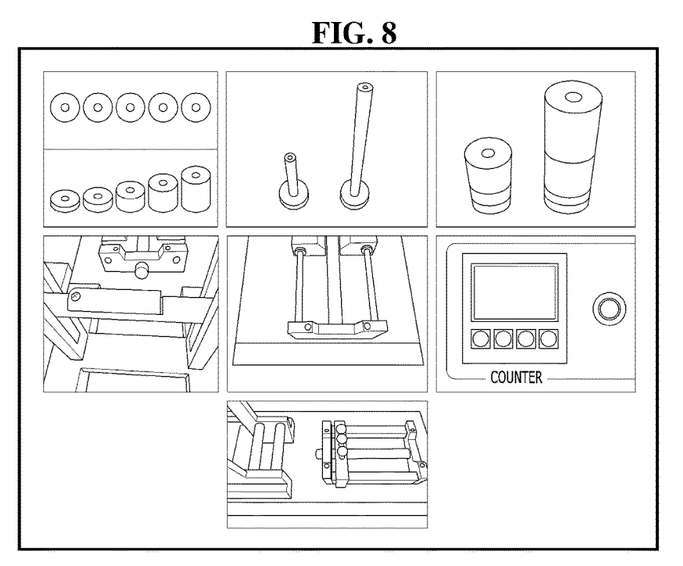
FIG. 8 is an experimental device for measuring tenacity in the present disclosure.

A device as shown in FIG. 8 was prepared to count the number of frictions until the cord yarn is cut and compare states of the threads after a predetermined number of frictions.

The rubber employed a 3M lapping film 15 micron. For the tension of the rubbed cord yarn, a weight of 50 gr was applied. In addition, the abrasion resistance is calculated as a value obtained by dividing the number of reciprocations until the test piece rubbed by the rubber is cut by a diameter of the test piece.

The cord yard prepared according to the present disclosure has abrasion resistance of 2 or above, up to 4. However, the cord yarn not belonging to the present disclosure was analyzed as having abrasion resistance lower than 2, and a cord yarn prepared by a general braiding method also had abrasion resistance lower than 2.

The high-strength cord yarn configured as above has uniformity, excellent roundness and small porosity and thus sufficiently meets specific strength and dimensional stability demanded by kite lines, parachute lines or fishing lines, in comparison to existing braided works, knitted products using a needle or general twisted products.

Example 1

Six strands of ultrahigh molecular weight polyethylene 45d/40f (d represents denier, and f represents filament) with a specific weight of 0.98 and tenacity of 30 g/d were prepared. Among them, one strand La first strand formed by twisting at least one first filament) had D1 of 0.0000806m, Thus, by applying twists (for forming a first strand) to the six strands to have K1 of 0.0027778/D1, the denier became 47.0d due to twist shrinkage, and K1 became 34 per meter.

Among the six strands, two strands had D2 of 0.0001165. By twisting the two strands (for forming second strand) to have a K2 value of 0.2147027/D2, the denier became 98d due to twist shrinkage, and the K2 value became 1,843 per meter.

To the remaining four strands, the number of twists corresponding to K2 was identically applied for every two strands, thereby making two strands, each having two strands (forming second strand).

Three strands (actually six strands) (a plurality of second strands) twisted as above had D3 of 0.0002018 meter, the denier became 304d by twisting to have a K3 value of 0.1837763/D3, and the K3 value was 911 per meter (forming the cord, yarn of the invention).

Second, the number of twists corresponding to K2 was simultaneously applied to one strand (a first strand) in the S direction and one strand (a first strand) in the Z direction, thereby making a single strand La second strand) in the S direction. In addition, the number of twists corresponding to K2 was also applied to one strand (a first strand) in the S direction and one strand (a first strand) in the Z direction, thereby making another single strand (a second strand) in the S direction. In this way, two strands (second strands) in the S direction were prepared simultaneously.

Third, the number of twists corresponding to K3 was applied to three strands (a plurality of second strands) in the S direction in the second step so that three strands are twisted simultaneously in the Z direction into a single strand (the cord yarn including a plurality of strands).

The second step and the third step were performed continuously.

The cord yarn prepared as above had roundness of 75% or above and porosity of 10% or below, which is excellent in dimensional stability.

In addition, the cord yarn prepared as above had abrasion resistance of 4.38, which is more excellent in comparison to abrasion resistance of a general braided product.

Figure 9:
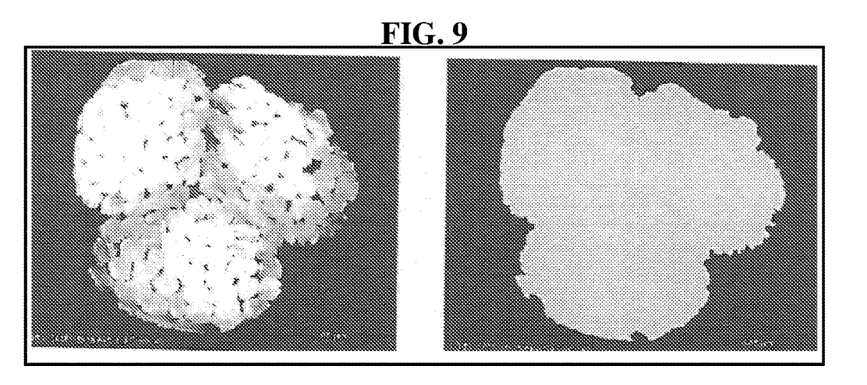
FIGS. 9 to 16 are projected sectional views and tables showing calculated roundness according to Examples 1 to 4 of the present disclosure.
Figure 10:
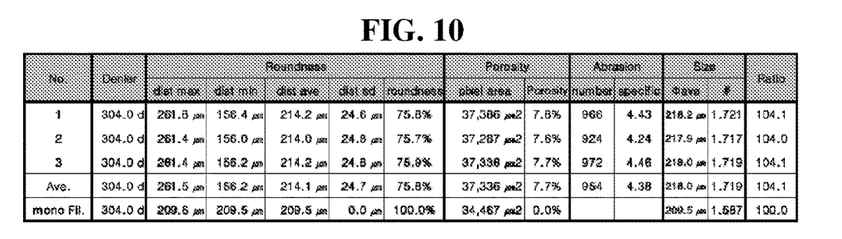

The above results may be found in the projected sectional view and the table of FIGS. 9 and 10.

Example 2

Eight strands of ultrahigh molecular weight polyethylene 25d/10f with specific weight of 0.98 and tenacity of 30/d were prepared. Among them, one strand had D1 of 0.0000601m. Thus, by applying twists to the eight strands to have K1 of 0.0561266/D1, the denier became 25.75d due to twist shrinkage, and the K1 value became 934 per meter.

Among them, two strands had D2 of 0.0000863 meter, By twisting the two strands to have a K2 value of 0.1351145/D2, the denier became 51.5d due to twist shrinkage and the K2 value because 1,567 per meter.

To the remaining six strands, the number of twists corresponding to K2 was identically applied for every two strands, thereby making three strands, each having two strands.

Four strands (actually eight strands) twisted as above had D3 of 0.0001725 meter. In addition, the denier became 232d by twisting to have a K3 value of 0.1158553/D3, and the K3 value was 672 per meter.

Regarding the twisting direction, when eight strands are twisted at the first, four strands were twisted in the S direction, and four strands were twisted in the Z direction.

Second, the number of twists corresponding to K2 was simultaneously applied to one strand in the S direction and one strand in the Z direction, thereby making a single strand in the S direction. In addition, for the remaining strands, the number of twists corresponding to K2 was also applied to one strand in the S direction and one strand in the Z direction, thereby making another single strand in the S direction. In this way, three strands in the S direction were prepared simultaneously.

Third, the number of twists corresponding to K3 was applied to four strands of the S direction in the second step so that the four strands are twisted simultaneously in the Z direction into a single strand.

The second step and the third step were performed continuously.

The cord yarn prepared as above had roundness of 50.0% or above and porosity lower than 10.0%, which is excellent in dimensional stability. In addition, the prepared cord yarn had excellent abrasion resistance of 3.73.

Figure 11:
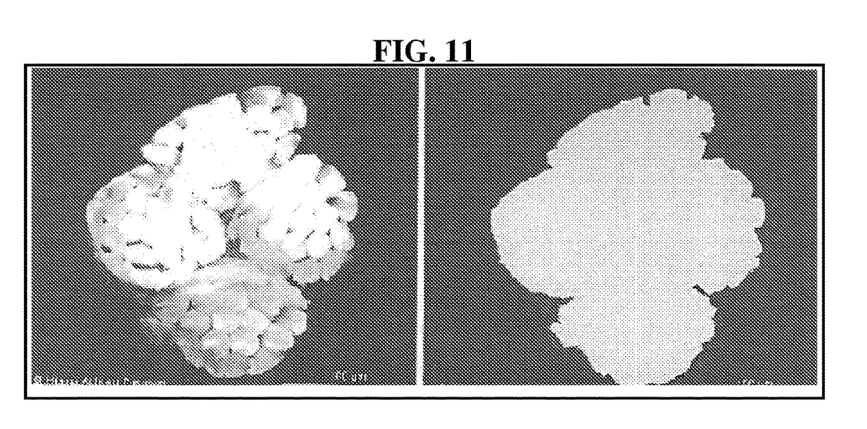
Figure 12:
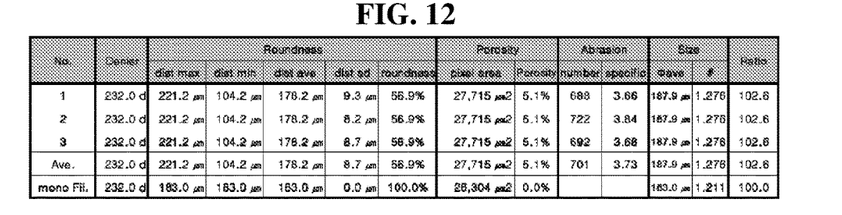

The above results may be found in the projected sectional view and the table of FIGS. 11 and 12.

Example 3

Four strands of ultrahigh molecular weight polyethylene 12d/8f with a specific eight of 0.98 and tenacity of 30 g/d were prepared. Among there, one strand had D1 of 0.0000416m. Thus, by applying twists to the four strands to have K1 of 0.0561266/D1, the denier became 13d due to twist shrinkage, and K1 became 1,348 per meter.

Among the four strands, two strands had D2 of 0.0000613 meter. By twisting the two strands to have a K2 value of 0.2228830/D2, the denier became 27d due to twist shrinkage and the K2 value became 3,637 per meter.

The number of twists corresponding to K2 was applied to the remaining two strands, thereby making one strand.

Two strands (actually four strands) twisted as above had D3 of 0.0000867 meter, the denier was 57d by twisting to have a K3 value of 0.1837763/D3, and the K3 value was 2,120 per meter.

Regarding the twisting direction, when four strands are twisted at the first, two strands were twisted in the S direction, and two strands were twisted in the Z direction Second, the number of twists corresponding to K2 was simultaneously applied to one strand in the S direction and one strand in the Z direction, thereby making a single strand in the S direction. In addition, for the remaining strands, the number of twists corresponding to K2 was also applied to one strand in the S direction and one strand in the Z direction, thereby making a single strand in the S direction.

Third, the number of twists corresponding to K3 was applied to two strands of the S direction in the second step so that two strands are twisted simultaneously in the Z direction into a single strand.

The second step and the third step were performed continuously.

The cord yarn prepared as above had roundness of 50.0% or above and porosity of 20.0% or below, which is excellent in dimensional stability. In addition, the prepared cord yarn had excellent abrasion resistance of 2.30.

Figure 13:
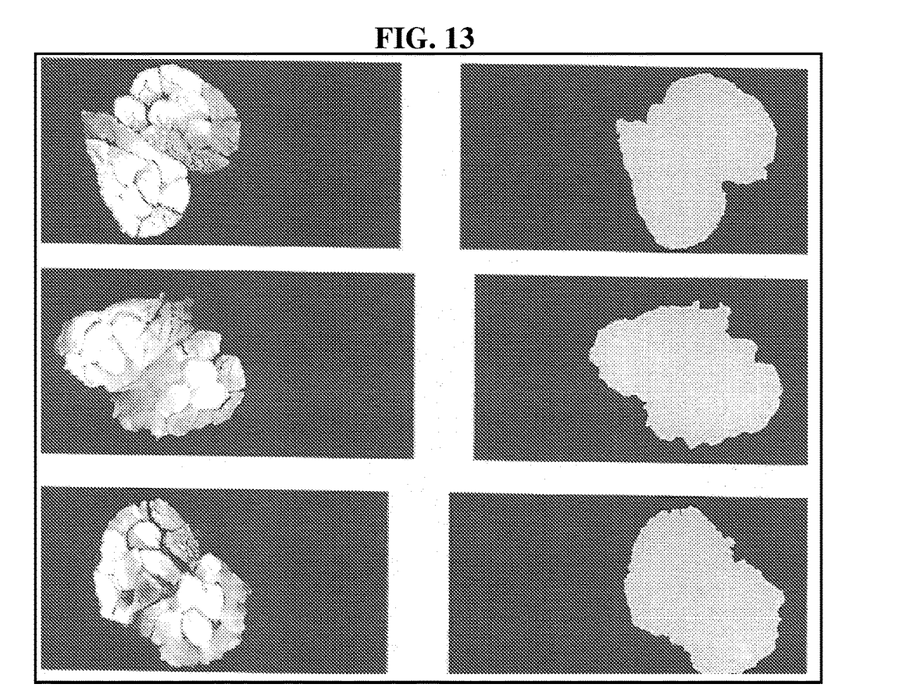
Figure 14:
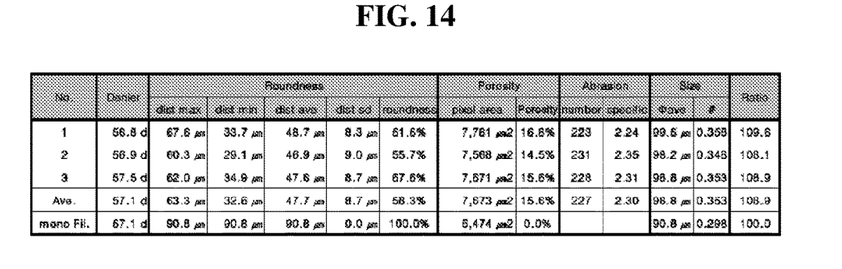

The above results may be found in the projected sectional view and the table of FIGS. 13 and 14.

Example 4

One piece of stainless steel of 304L and 0.065 mm and one piece of nylon 6,12 copolymer 20d/2f 1 having a melting point of 80° C. and serving as a hot melt yarn for preventing slipping with respect to a polyethylene yarn were fixed deeply to the core of Example 1 to a point where a twist starts, and then thermally melted at 120° C.

The K1, K2 and K3 values, the number of twists and the twisting direction were identical to those of Example 1.

The cord yarn prepared as above had roundness of 64% or above and porosity lower than 20.0%, which is excellent in dimensional stability. In addition, the prepared cord yarn had excellent abrasion resistance of 2.57.

Figure 15:
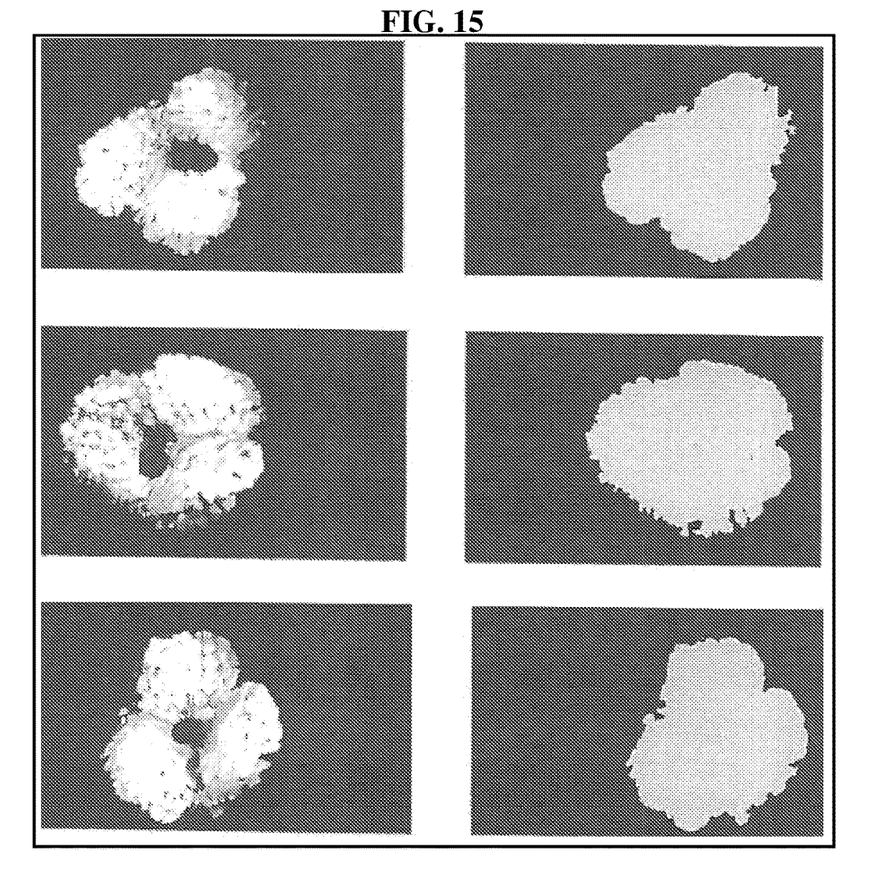
Figure 16:
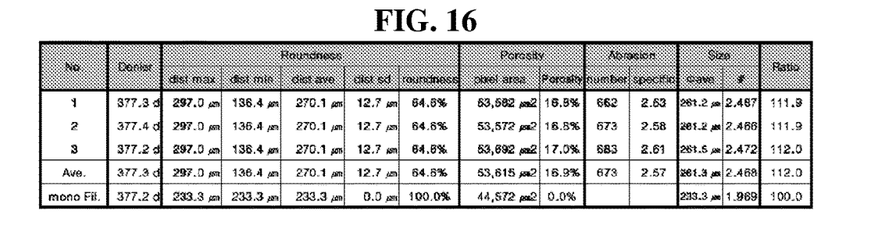

FIGS. 15 and 16 show data obtained from the test piece prepared by Example 4 through three measurements.

Comparative Example 1

Six strands of ultrahigh molecular weight polyethylene 45d/40f with specific weight of 0.98 and tenacity of 30 g/d were wound around a braid bobbin and then tightly braided by a general braiding machine at RPM 220 with the number of twists of 33 per inch.

As shown from the results, in spite of tight braiding, the obtained cord yarn had roundness lower than 50% and porosity lower than 60%. In addition, the cord yarn of Comparative Example 1 having a thickness similar to the cord yarn of Example 1 had bad abrasion resistance of 1.75.

Figure 17:
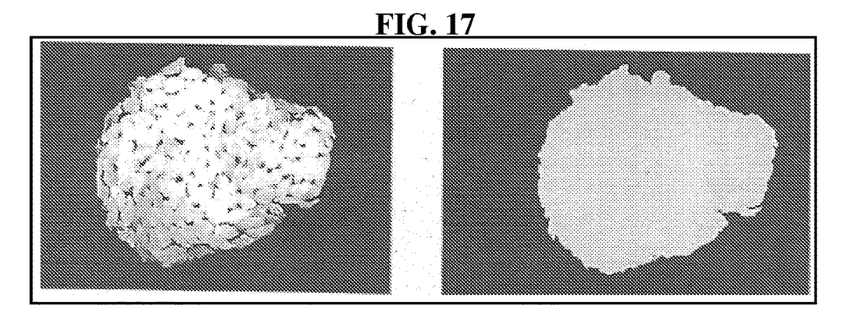
FIGS. 17 to 22 are projected sectional views and tables showing calculated roundness according to Comparative Examples 1 to 3 of the present disclosure.
Figure 18:
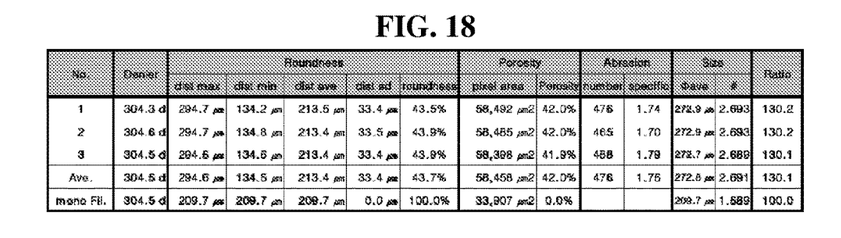

FIGS. 17 and 18 show data obtained from the test piece prepared by Comparative Example 1 through three measurements.

Comparative Example 2

The twist of the first step was not applied to six strands of ultrahigh molecular weight polyethylene 45d/40f with specific weight of 0.98 and tenacity of 30 g/d.

Among them, two strands had D2 of 0001165 meter. By twisting the two strands to have a K2 value of 02147027/D2, the denier became 98d due to twist shrinkage, and the K2 value became 1,843 per meter.

To the remaining four strands, the number of twists corresponding to K2 was identically applied for every two strands, thereby making two strands, each having two strands.

Three strands (actually six strands) twisted as above had D3 of 0.0002018 meter. In addition, the denier became 304.5d by twisting to have a K3 value of 0.1837763/D3, and the K3 value was 911 per meter.

Second, the number of twists corresponding to K2 was simultaneously applied to one strand in the S direction and one strand in the Z direction, thereby making a single strand in the S direction. In addition, for the remaining strands, the number of twists corresponding to K2 was also applied to one strand in the S direction and one strand in the Z direction, thereby making a single strand in the S direction. In this way, two strands in the S direction were prepared simultaneously.

Third, the number of twists corresponding to K3 was applied to three strands in the S direction in the second step so that the three strands are twisted simultaneously in the Z direction into a single strand.

The second step and the third step were performed continuously. The cord yarn prepared as above had roundness of 50.0% or above and porosity of 40% or above. In addition, the prepared cord yarn had abrasion resistance of 1.92, which is lower than a standard quality level, due to the absence of the twist of the first step.

Figure 19:
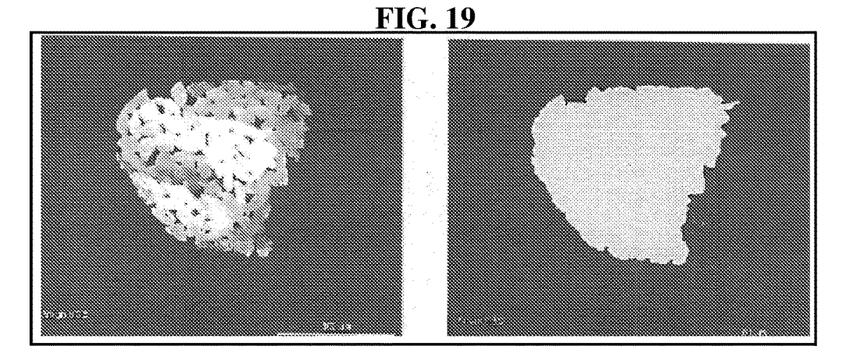
Figure 20:
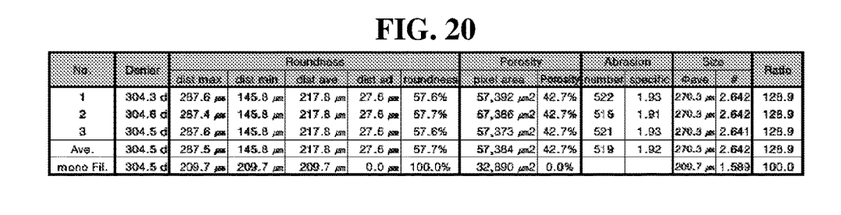

FIGS. 19 and 20 show data obtained from the test piece prepared by Comparative Example 2 through three measurements.

Comparative Example 3

Six strands of ultrahigh molecular weight polyethylene 45d/40f with specific weight of 0.98 and intensity tenacity of 300 were prepared. Among them, one strand had D1 of 0.0000806m. Thus, by applying twists to the six strands to have K1 of 0.0027778/D1, the denier became 47.0d due to twist shrinkage, and the K1 value became 34 per meter.

Among them, two strands had D2 of 0.0001165 meter. By twisting the two strands to have a K2 value of 0.0111156/D2, the denier became 95d, and the K2 value became 95 per meter.

To the remaining four strands, the number of twists corresponding to K2 was identically applied for every two strands, thereby making two strands, each having two strands.

Three strands (actually six strands) twisted as above had D3 of 0.0002029 meter. In addition, the denier became 301.5d by twisting to have a K3 value of 0.0222584/D3, and the K3 value was 110 per meter.

Second, the number of twists corresponding to K2 was simultaneously applied to one strand in the S direction and one strand in the Z direction, thereby making a single strand in the S direction. In addition, for the remaining strands, the number of twists corresponding to K2 was also applied to one strand in the S direction and one strand in the Z direction, thereby making a single strand in the S direction. In this way, two strands in the S direction were prepared simultaneously.

Third, the number of twists corresponding to K3 was applied to three strands in the S direction in the second step so that the three strands are twisted simultaneously in the Z direction into a single strand.

The second step and the third step were performed continuously.

The cord yarn prepared as above had roundness lower than 40% and porosity of 40% or above, which has bad dimensional stability.

In addition, after analyzing the cord yard with an abrasion resistance tester, prepared by the inventor, it may be found that abrasion resistance is very bad.

Figure 21:
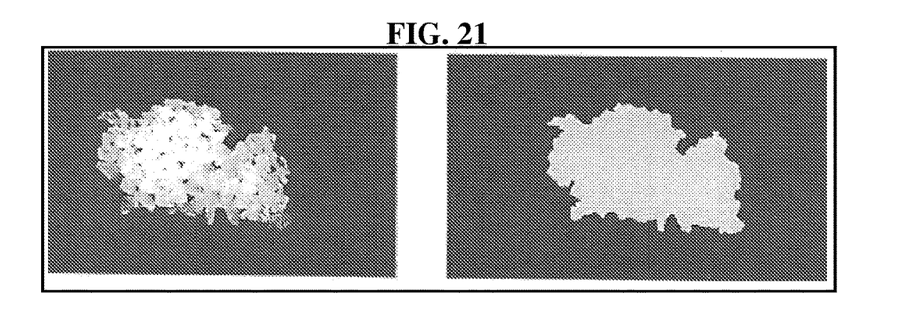
Figure 22:
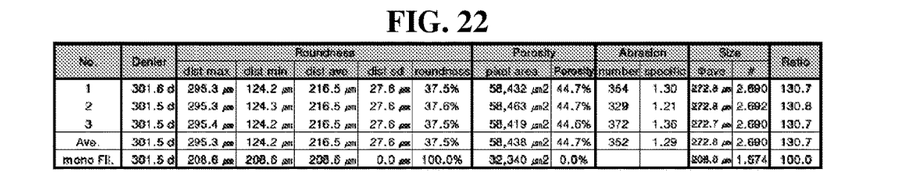
Figure 23:
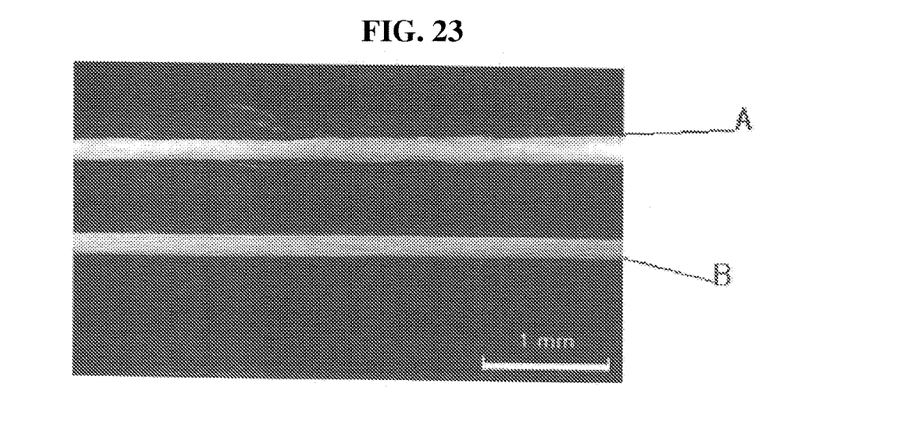
FIG. 23 is a photograph showing tenacity of Comparative Example 3 after experiment.

FIGS. 21 and 22 show data obtained from the test piece prepared by Comparative Example 3 through three measurements, FIG. 23A is a photograph showing the cord yarn prepared according to Comparative Example 3 after the test piece was reciprocated 100 times, and FIG. 23B is a photograph showing the cord yarn prepared according to Example 3 after the test piece was reciprocated 100 times.

| Reference Symbols | |
|---|---|
| A: multi or mono filament | D1: diameter (m) of a fiber A |
| K1: the number of braids (/m) per unit length | 1/K1: length (m) of one braid |
| | πD: circumference of a fiber A |
| Θ1: braid angle | |

What is claimed is:

1. A method for manufacturing a cord yarn having improved stability formed by twisting a plurality of strands, the method comprising:
    applying a first twist at a first twisting step to at least one first filament for forming a first strand so that a K1 value has a value of 0.1837763/D1 or below;
    applying a second twist at a second twisting step to at least one first strand for forming a second strand so that a K2 value has a value between 0.0166819/D2 and 0.2670937/D2; and
    applying a third twist a third twisting step to a plurality of the second strands for forming the cord yarn so that a K3 value has a value between 0.0278485/D3 and 0.2228830/D3,
    wherein the twists are applied so that porosity between strands of the cord yarn is less than 40% and porosity=(A−B)/A×100

A: Sectional area of a cord yarn calculated using a measuring program;
    B: Sectional area of a mono filament having the same denier as a test piece (calculated with specific weight and denier), and
    wherein K1 is a number of twists per meter of said first twist, D1 is a diameter of the twisted first strand in meters at said first twist, K2 is a number of twists per meter at said second twist, D2 is a diameter of the twisted second strand in meters at said second twist, K3 is a number of twists per meter at said third twist, and D3 is a diameter of the twisted cord yarn in meters at said third twist.

2. The method for manufacturing a cord yarn according to claim 1,
    wherein before each twisting step, the filament is guided by a positioning device.

3. The method for manufacturing a cord yarn according to claim 1,
wherein in each twisting step, a twist is applied together with elongation of 1 to 20%.

4. The method for manufacturing a cord yarn according to claim 1,
wherein when the filament is a multi filament, fineness of a single filament is 0.5 denier to 100 denier, fineness of the entire filament is 3 denier to 2,400 denier, and a filament is any one of nylon, polyester, polyethylene including ultrahigh molecular weight polyethylene, aramid, p-phenylene benzobisoxazole (PBO), polyketon, polyacrylate fiber and polyvinyl alcohol (PVA) fiber which are 5 g/d or above in a breaking strength, and
wherein when the filament is a mono filament, fineness is 3 denier to 2,400 denier, and a filament is any one of nylon, polyester, polyethylene including ultrahigh molecular weight polyethylene, polyphenylene sulfide (PPS) and polyvinylidene fluoride (PVDF) which are 5 g/d or above in a breaking strength, and polytetrafluoroethylene (PTFE) which is 3 g/d or above in a breaking strength.

5. The method for manufacturing a cord yarn according to claim 1,
wherein when the filament is guided by a positioning device in any one of the twisting steps, at least one strand having a breaking strength of 2 g/d or above of PTFE melamine yarn, carbon fiber, metal thread and polymer thread fused at 200° C. or below is guided by the positioning device to be located at the center of the cord yarn.

6. A cord yarn having improved stability formed by twisting a plurality of strands, the cord yarn comprising:
a first twist to at least one first filament for forming a first strand so as to have a K1 value of 0.1837763/D1 or below;
a second twist to the at least one first strand for forming a second strand so as to have a K2 value between 0.0166819/D2 and 0.2670937/D2; and
a third twist to a plurality of the second strands for forming the cord yarn so as to have a K3 value between 0.0278485/D3 and 02968288/D3,
wherein K1 is a number of twists per meter at said first twist, D1 is a diameter of the twisted first strand in meters at said first twist, K2 is a number of twists per meter at said second twist, D2 is a diameter of the twisted second strand in meters at said second twist, K3 is a number of twists per meter at said third twist, and D3 is a diameter of the twisted cord yarn in meters at said third twist.

7. The cord yarn according to claim 6,
wherein when the filament is a multi filament, porosity between strands of the cord yarn is less than 40%, wherein
porosity=(A−B)/A×100
A: Sectional area of a cord yarn calculated using a measuring program;
B: Sectional area of a mono filament having the same denier as a test piece (calculated with specific weight and denier).

8. The cord yarn according to claim 7,
wherein at least one strand having a breaking strength of 2 g/d or above of PTFE, melamine yarn, carbon fiber, metal thread or polymer thread fused at 200° C. or below is located at the center of the cord yarn to allow specific weight adjustment, fusion, or both specific weight adjustment and fusion.

9. The cord yarn according to claim 6,
wherein the cord yarn or a product obtained by coating, water-repelling or silicon-treating the cord yarn is used for fabric, knit works, strings, fishing lines, ropes, accessories for mobile phones, floss, parachute cords or lines for adjusting blinds.

10. The method for manufacturing a cord yarn according to claim 2,
wherein when the filament is a multi filament, fineness of a single filament is 0.5 denier to 100 denier, fineness of the entire filament is 3 denier to 2,400 denier, and a filament is any one of nylon, polyester, polyethylene including ultrahigh molecular weight polyethylene, aramid, p-phenylene benzobisoxazole (PBO), polyketon, polyacrylate fiber and polyvinyl alcohol (PVA) fiber which are 5 g/d or above in a breaking strength, and
wherein when the filament is a mono filament, fineness is 3 denier to 2,400 denier, and a filament is any one of nylon, polyester, polyethylene including ultrahigh molecular weight polyethylene, polyphenylene sulfide (PPS) and polyvinylidene fluoride (PVDF) which are 5 g/d or above in a breaking strength, and polytetrafluoroethylene (PTFE) which is 3 g/d or above in a breaking strength.

11. The method for manufacturing a cord yarn according to claim 3,
wherein when the filament is a multi filament, fineness of a single filament is 0.5 denier to 100 denier, fineness of the entire filament is 3 denier to 2,400 denier, and a filament is any one of nylon, polyester, polyethylene including ultrahigh molecular weight polyethylene, aramid, p-phenylene benzobisoxazole (PBO), polyketon, polyacrylate fiber and polyvinyl alcohol (PVA) fiber which are 5 g/d or above in a breaking strength, and
wherein when the filament is a mono filament, fineness is 3 denier to 2,400 denier, and a filament is any one of nylon, polyester, polyethylene including ultrahigh molecular weight polyethylene, polyphenylene sulfide (PPS) and polyvinylidene fluoride (PVDF) which are 5 g/d or above in a breaking strength, and polytetrafluoroethylene (PTFE) which is 3 g/d or above in a breaking strength.

12. The method for manufacturing a cord yarn according to claim 2,
wherein when the filament is guided by a positioning device in any one of the twisting steps, at least one strand having a breaking strength of 2 g/d or above of PTFE melamine yarn, carbon fiber, metal thread and polymer thread fused at 200° C. or below is guided by the positioning device to be located at the center of the cord yarn.

13. The method for manufacturing a cord yarn according to claim 3,
wherein when the filament is guided by a positioning device in any one of the twisting steps, at least one strand having a breaking strength of 2 g/d or above of PTFE melamine yarn, carbon fiber, metal thread and polymer thread fused at 200° C. or below is guided by the positioning device to be located at the center of the cord yarn.

14. The cord yarn according to claim 7,
wherein the cord yarn or a product obtained by coating, water-repelling or silicon-treating the cord yarn is used for fabric, knit works, strings, fishing lines, ropes, accessories for mobile phones, floss, parachute cords or lines for adjusting blinds.

15. The cord yarn according to claim 8, wherein the cord yarn or a product obtained by coating, water-repelling or silicon-treating the cord yarn is used for fabric, knit works, strings, fishing lines, ropes, accessories for mobile phones, floss, parachute cords or lines for adjusting blinds.

* * * * *